United States Patent
Schaffar et al.

(10) Patent No.: US 7,815,788 B2
(45) Date of Patent: *Oct. 19, 2010

(54) CREATININE SENSOR CALIBRATION

(75) Inventors: Bernhard Schaffar, Graz (AT); Herbert Kroneis, Graz (AT); Taghi Noormofidi, Graz (AT); Gernot Florian, Graz (AT); Wolf-Dietrich Steinbock, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/057,636

(22) Filed: Mar. 28, 2008

(65) Prior Publication Data

US 2008/0173064 A1    Jul. 24, 2008

Related U.S. Application Data

(63) Continuation of application No. 10/344,499, filed on Nov. 26, 2003, now Pat. No. 7,371,314.

(30) Foreign Application Priority Data

Aug. 11, 2000 (AT) .............................. A 1391/2000
Aug. 9, 2001 (WO) ....................... PCT/AT01/00265

(51) Int. Cl.
*G01N 27/327*    (2006.01)
(52) U.S. Cl. .................................. 205/777.5; 205/792
(58) Field of Classification Search ........................ 204/403.01–403.15; 205/777.5, 778, 792
See application file for complete search history.

(56) References Cited

U.S. PATENT DOCUMENTS

| | | | | |
|---|---|---|---|---|
| 4,121,905 A | * | 10/1978 | Maurukas | 436/16 |
| 4,812,399 A | * | 3/1989 | Mauck et al. | 435/18 |
| 5,120,420 A | * | 6/1992 | Nankai et al. | 204/403.11 |
| 5,173,165 A | * | 12/1992 | Schmid et al. | 204/403.1 |
| 5,281,536 A | * | 1/1994 | Wild et al. | 436/16 |
| 5,527,706 A | * | 6/1996 | Kroneis et al. | 436/55 |

(Continued)

FOREIGN PATENT DOCUMENTS

GB    2 185 318 A    1/1987

(Continued)

OTHER PUBLICATIONS

English language translation of Miyashiro JP58061459 A, May 2007.*

(Continued)

*Primary Examiner*—Alex Noguerola
(74) *Attorney, Agent, or Firm*—McDonnell Boehnen Hulbert & Berghoff LLP

(57) ABSTRACT

In a method for calibrating a biosensor for the amperometric determination of creatinine in biological liquids, consisting of one electrode system each for measuring the concentrations of creatinine and creatine, with at least two calibration solutions being used, the electrode system for measuring the creatinine concentration is calibrated with a creatinine solution which, prior to the calibration measurement, was mixed in the form of an acidic solution with an alkaline buffer solution, and the electrode system for measuring the creatine concentration is calibrated with a solution in which creatinine and creatine are at a thermodynamic equilibrium.

20 Claims, 1 Drawing Sheet

U.S. PATENT DOCUMENTS 5,874,078 A * 2/1999 Hongo et al. .............. 424/94.4
7,371,314 B2 * 5/2008 Schaffar et al. ............. 205/792

FOREIGN PATENT DOCUMENTS

JP          58061459         12/1983
JP          60151560          9/1985

OTHER PUBLICATIONS

Edgar et al. ("Equilibrium between creatine and creatinine in aqueous solution. The effect of hydrogen ion," Journal of the American Chemical Society (1925), 47, 1179-88).*

Wikipedia entries for "Good's buffers" and "MES" downlo9aded Apr. 24, 2007.*

* cited by examiner

CREATININE SENSOR CALIBRATION

CROSS-REFERENCE TO RELATED APPLICATIONS

This application is a continuation of U.S. patent application Ser. No. 10/344,499 filed 26 Nov. 2003 (now U.S. Pat. No. 7,371,314 B2), which is a National Phase entry of PCT Application No. PCT/AT01/00265 filed 9 Aug. 2001, which claims priority to Austrian Patent Application No. A 1391/2000 filed 11 Aug. 2000, all of which are incorporated herein by reference.

FIELD OF THE INVENTION

The invention relates to a method for calibrating a biosensor for the amperometric determination of creatinine in biological liquids, consisting of one electrode system each for measuring the concentrations of creatinine and creatine, with at least two calibration solutions being used. A

BACKGROUND OF THE INVENTION

The determination of enzymatically degradable substances; such as creatinine, glucose etc., by means of sensors in biological liquids, for example in blood, urine, plasma, serum and liquor, is preferably carried out via biosensors comprising immobilized enzymes. From the literature, several electrochemical and photometric methods of determining those substances are known.

In that way, creatinine may be potentiometrically determined, for example by means of the enzyme creatinine deiminase, involving a subsequent determination of the ammonium content. Another method consists in determining the creatinine concentration by means of an enzyme cascade using the enzymes creatininase, creatinase and sarcosine oxidase, with hydrogen peroxide ($H_2O_2$) being finally measured at an amperometric electrode (Tsuchida, T., Yoda, K., Clin. Chem. 29/1, 51-55 (1983)).

The invention relates to a method for calibrating biosensors that function in accordance with the last-mentioned principle. The conversion of creatinine to hydrogen peroxide is carried out according to the following reaction steps:

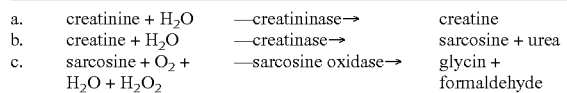

| a. | creatinine + $H_2O$ | —creatininase→ | creatine |
| b. | creatine + $H_2O$ | —creatinase→ | sarcosine + urea |
| c. | sarcosine + $O_2$ + $H_2O$ + $H_2O_2$ | —sarcosine oxidase→ | glycin + formaldehyde |

In order to be able to faultlessly determine the creatinine in a biological sample, it is necessary to correct the results of the creatinine system that consists of an electrode system comprising all three enzymes by those of the creatine system the electrode system of which comprises only the enzymes creatinase and sarcosine oxidase, since in biological samples creatinine and creatine usually coexist and, according to the system, the creatinine system is only capable of recognizing the sum of creatinine and creatine.

Thus, for a calibration of the biosensor, solutions for calibrating the creatinine, system as well as the creatine system are necessary.

The calibration of a biosensor for the determination of creatinine is aggravated further by the fact that creatinine and creatine are at an equilibrium if the solution has room temperature and a neutral pH, i.e., neither of the two dissolved analytes can, on its own, be maintained at a stable concentration, which, however, would be absolutely necessary for calibrating the electrode systems.

Therefore, the user of the biosensor is forced to freshly prepare the calibration solution(s) before measuring takes place by weighing creatinine and/or creatine into a vessel and dissolving the weighed portion in a certain amount of buffer liquid. It is indeed true that, at room temperature, said solution(s) is (are) sufficiently stable for a short period of time, in general for about a week, since the conversion of creatinine to creatine or vice versa proceeds very slowly, however, the preparation procedure must be repeated after that time period.

Said method is disadvantageous in that the continuous, at least weekly, fresh preparation or the calibration solutions prevents the calibration from being carried out at any time in a quick, simple and topically flexible manner. Furthermore, repeated weighing-in and dissolving with the purpose of securing a sufficiently high accuracy require a larger consumption of creatinine and/or creatine and of buffer liquid.

SUMMARY OF THE INVENTION

The invention has as its object to provide a method of the initially described kind, overcoming the above mentioned drawbacks. In particular, the method according to the invention is supposed to provide calibration solutions which do not have to be prepared on a weekly basis by weighing-in and for the preparation of which a smaller amount of base material is necessary, based on the number of applications, in comparison with the prior art. In addition, it must be possible to prepare the calibration solutions in a quick and simple manner and practically anywhere.

According to the invention, said object is achieved in that the electrode system for measuring the creatinine concentration is calibrated with a creatinine solution which, prior to the calibration measurement, was mixed in the form of an acidic solution with an alkaline buffer solution, and in that the electrode system for measuring, the creatine concentration is calibrated with a solution in which creatinine and creatine are at a thermodynamic equilibrium.

DETAILED DESCRIPTION OF THE INVENTION

Figure 1:
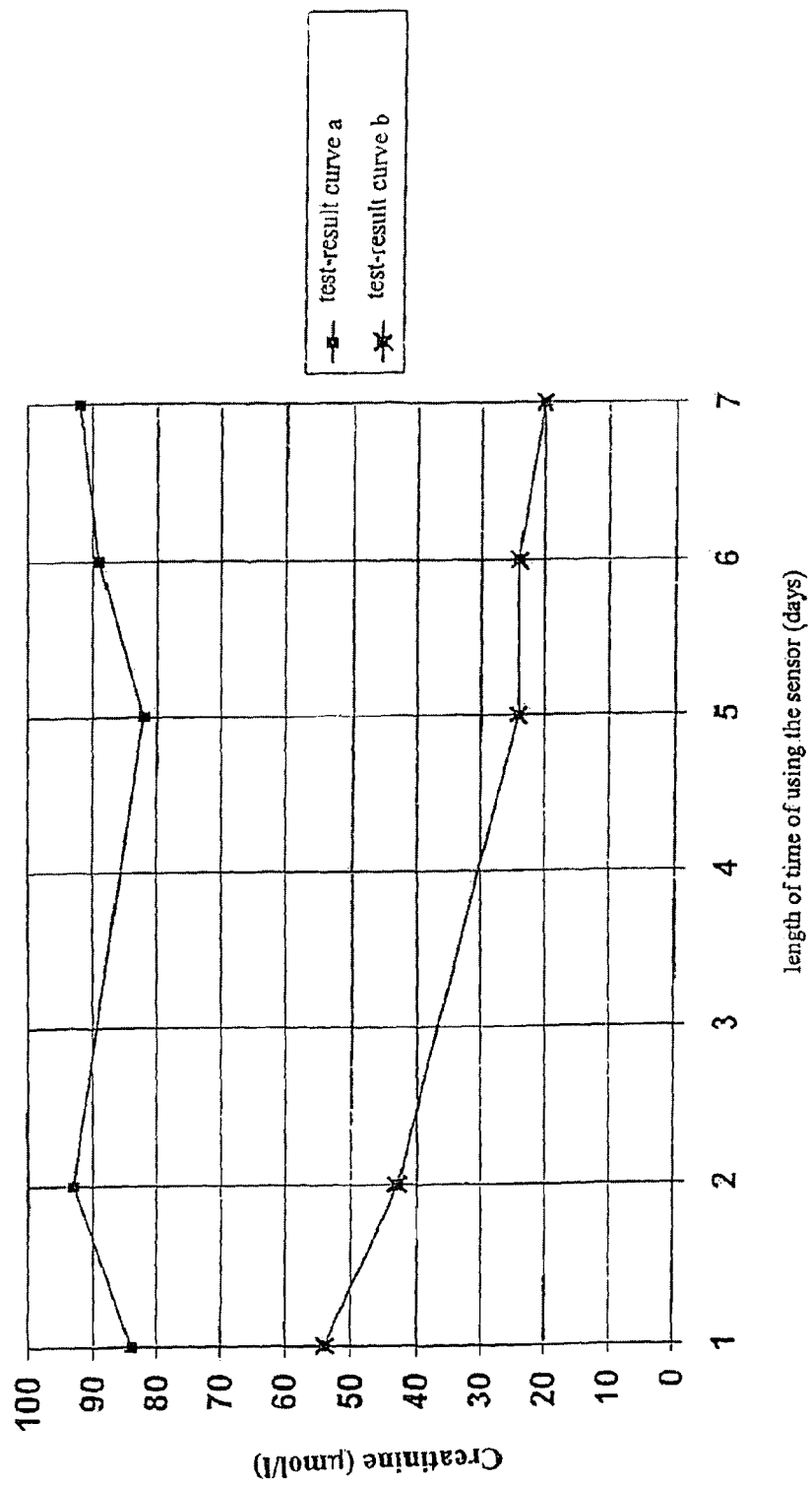
FIG. 1 shows a) the test-result curve for a creatinine sensor which was calibrated by means of a solution containing 40 mM of acetate, and b) the test-result curve of a creatinine sensor calibrated without the addition of all inhibitor to the calibration solution, over a time period of one week.

From J. Am. Chem. Soc. 47, 1179-1188, 1925 (G. Edgar, H. E. Shiver) it is known that, with an increasing temperature and an increasing concentration of hydrogen ions, the creatine/creatinine equilibrium shifts toward the creatinine.

According to Biochem. J., 920-929, 1928 (R. K. Cannan, A. Shore), the speed of the equilibrium reaction creatine⇌creatinine in a strongly acidic solution is proportional to the concentration of hydrogen ions. In acidic solutions of roughly pH 3 (f.i. 2<pH<4), the conversion of creatine to creatinine is substantially irreversible.

The invention makes use of the fact that it is feasible to keep dissolved creatinine substantially stable if the pH of the solution is within the acidic range. It is true that biosensors can no longer be calibrated with such a solution, since both the activity and the lifetime of the sensor are greatly reduced in such an acidic environment, but a creatinine calibration solution may be readily produced by mixing a small amount of said acidic solution with a solution consisting of slightly alkaline buffering, salts, which creatinine calibration solution also is sufficiently stable at room temperature for at least a week and may then be replaced by a new mixture of an acidic creatinine solution and an alkaline buffer solution, without having to weigh in any creatinine.

Preferably, a creatinine solution having a pH of from 2 to 4, more preferably from 2.5 to 3, is used as the acidic solution.

Mixing the acidic creatinine solution with the alkaline buffer solution may be carried out, for instance, automatically in a device in which the biosensor is integrated and operated. For that purpose, it is merely necessary to fill at larger time intervals the vessels intended for receiving the solutions by freshly prepared solutions.

By means of the creatinine calibration solution produced according to the invention, it is feasible to unequivocally calibrate the electrode system intended for measuring the creatinine concentration. It is feasible to separately determine and withdraw any creatine possibly formed after a certain amount of time by determining it by means of an already calibrated sensor.

On the other hand, the electrode system for measuring the creatine concentration is calibrated by means of a neutral solution in which creatinine and creatine are provided at the equilibrium concentrations known for a certain temperature. In addition, by means of said solution, the effect of the creatine on the creatinine system may be determined indirectly or may be calibrated, respectively.

Upon mixing the creatinine solution and the buffer solution, the exact creatinine concentration of the creatinine calibration solution preferably is calculated by the aid of a ionic tracer only weighed into one of the two mixing components. By checking the mixing ratio by means of the ionic tracer, the exact creatinine content of the mixture, i.e. of the calibration solution, may be calculated via the known concentration of the weighed portion.

Furthermore, it is advantageous if interfering substances present in the liquids to be examined, for example, enzyme inhibitors and/or inhibitors having a similar effect on the enzymes such as those present in the liquids to be examined—such inhibitors have an advantage in that they may be introduced into reagents in a stable manner—are added to the calibration solutions at their average concentrations such as to be able to also take their effects on the measuring results into account and hence to improve the measuring result.

Many biological liquids contain bicarbonate. From J. Mol. Biol. 214, 597-610, 1990 (M. Coll et al), it is known that bicarbonate acts as an inhibitor creatinase. It therefore is advantageous to add bicarbonate as an interfering substance, i.e. a competitive inhibitor, to the calibration solutions.

However, it has been shown that the measuring behaviour of biosensors is particularly good if acetate as a competitive inhibitor is added to the calibration solutions. Contrary to bicarbonate, acetate may advantageously be kept stable in a solution at a neutral pH.

In Tables 8-10, the effect of a bicarbonate and acetate interference in the calibration solutions on the measuring behaviour of creatine and creatinine sensors is illustrated. Table 8 shows the measuring results for an aqueous solution, consisting of about 120 μM of creatinine and 210 μM of creatine, corresponding to a creatinine ratio Cal 2 (see example), which was subjected to a measurement a) without any interfering substances, b) under the addition of 40 mmol/l of acetate and c) the addition of 25 mmol/l of bicarbonate. The measurement was carried out, on the one hand, by means of a biosensor which was calibrated under the addition of 40 mmol/l of acetate and, on the other hand, by means of a sensor which was calibrated without the additions of any acetate.

In analogy thereto, Table 9 shows the measuring results of the creatinine sensors for an aqueous solution containing 230 μM of creatinine, corresponding to a calibration ratio Cal 1 (see below).

Both tables show that it is well possible to compensate for the bicarbonate interference in the measuring solution by means of acetate. That finding is, also pointed out by the results of Table 10. Here, various control agents containing bicarbonate were measured by means of the above mentioned biosensors which had been calibrated with and without the addition of acetate. The measuring results of the sensors calibrated under the addition of acetate are, on an average, higher by about 40% and correspond with the required values of the control agents better than those of the sensors calibrated without the addition of acetate.

FIG. 1 shows a) the test-result curve for a creatinine sensor which was calibrated by means of a solution containing 40 mM of acetate, and b) the test-result curve of a creatinine sensor calibrated without the addition of an inhibitor to the calibration solution, over a time period of one week. According to test-result curve b, the creatinine concentration of about 90 μM in the measuring solution (bicarbonate-containing bovine serum) is evaluated to be at only 54 μM already on the first day, which is due to all interference that was not counterbalanced during the calibration of the sensor as well as the natural degradation of the enzyme, and decreases to about 20 μM in the course of one week. Test-result curve a, on the other hand, remains for one week in the range of from 82 to 92 μM, which corresponds very well with the true value.

Suitably, the calibration solutions are mixed with biocides such as isothiazolone, derivatives, and/or a combination of biocides and antibiotics, which additives effect a stabilization of the solutions. Isothiazolone derivatives to be used in this respect are, for instance, 2-methyl-2,3-dihydroisothiazole-3-one, 5-chloro-2-methyl-2,3-dihydroisothiazole-3-one or 2-n-octyl-2,3-dihydroisothiiazole-3-one. Usable antibiotics are, for instance, ciprofloxacin or gentamicin. The sensor systems are not impaired when using said substances at effective concentrations.

Amine buffers according to Norman Good or bicarbonate are preferably used as buffers for alkaline buffer solutions. Lactate/lactic acid (see, f.i., Table 1) and amine buffers according to Norman Good are suitable as buffers for acidic solutions, if they exhibit sulfonic acid groups (f.i. HEPES or MOPS; see Tables 2 and 3).

By varying the electrolyte and buffer systems in the calibration solutions, physiological conditions such as pH, buffer capacity, ionic environment and ionic strength may be adjusted arbitrarily to those of the biological liquids to be examined.

In the following, the invention is illustrated further by means of the following example:

EXAMPLE

Formulation of Calibration Solutions for Calibrating Creatinine and Creatine Systems and/or the Electrochemical Interference In the following tables 1-6, variants for the formulation of calibration solutions, which are adjusted to the calibration of creatinine and creatine, are listed up.

The calibration solution for the calibration of creatinine is derived from: Creatinine solution Cal 1 (acidic) and buffer solution Cal 1 (alkaline) after a 1:1-mixture (assay of the mixing ratio by $K^+$)

In the tables, the calibration solution for the calibration of creatine is denoted by Cal 2.

The formulations listed in Tables 4-6 may also be used for the calibration of other substances existing in biological liquids (as indicated).

Variant 2 (Cal 2) is advantageous, for example, if calibration components are to be included which are more stable either in an acidic or in an alkaline environment than in a finished calibration solution (f.i. glucose). A further advantage of said variant consists in that the concentration ratios between creatinine and creatine may be varied.

Also in Variant 3 (Cal 1), more degrees of freedom are possible when adapting the calibration solution to any physiological conditions.

Examples of the washing or zero-point calibration solution, which furthermore is necessary for calibrating a sensor and which does not contain any of the substances to be determined and hence provides for the evaluation of the "background signal" or the "zero-point line", respectively; of the sensor, are indicated in Table 7. As with the calibration solutions, the quantitative composition of said solution may be adapted to the conditions to be found in the biological sample, such as shown by the indicated variants.

For stabilizing the enzymes which are necessary for carrying out the creatinine measurement, the standby solution preferably contains $MgNa_2EDTA$, whereby in this case an amount of 0.5 mM is sufficient. However, also amounts of up to 5 mM of $MgNa_2EDTA$ are conceivable for the purpose of stabilization. With combined-analysis devices, which also carry out a measurement of Ca and Mg, larger amounts of $MgNa_2EDTA$ may have detrimental effects, however. Instead of $MgNa_2EDTA$, hypophosphitic may also be used as a stabilizer (Tsuchida, T, Yoda, K., ClinChem. 29/1, 51-55 (1983)).

The solution according to Variant 1 may be used additionally as a calibration solution for the calibration of $NH_4^+$ and urea sensors. The other parameters (ionic strength, ionic environment, etc.) are close to the physiological standard values; the buffer capacity is increased.

Variant 2 also contains solution components, which, in terms of their amounts, are adapted to the physiological standard values, with the buffer capacity being lower than that of Variant 1.

In Variant 3, buffer capacity and ionic strength are substantially increased.

TABLE 1

| Substance | | Cal 1 acidic | Cal 1 alkaline | Cal 2 | Electrochemical interference |
|---|---|---|---|---|---|
| creatinine | [mmol/l] | 0.50 | — | 0.25 | — |
| creatine | [mmol/l] | — | — | 0.42 | — |
| Na-lactate | [mmol/l] | 6.20 | — | 15.0 | — |
| Na-acetate | [mmol/l] | — | 49.8 | 15.5 | — |
| HCl | [mmol/l] | 6.00 | — | — | — |
| NaOH | [mmol/l] | — | 50.0 | 22.5 | 22.5 |
| H-HEPES$^{(\pm)}$ | [mmol/l] | — | 81.2 | 41.5 | 41.5 |
| KCl | [mmol/l] | — | 10.0 | 8.00 | 5.00 |
| NaCl | [mmol/l] | 143.8 | 50.2 | 97.0 | 99.0 |
| Paracetamol | [mmol/l] | — | — | — | 1.00 |
| pH (37° C.) | [pH-units] | 3.00 | 7.51 | 7.38 | 7.38 |

| Resulting Cal 1 after 1:1-mixture | | |
|---|---|---|
| $Na^+$ | [mmol/l] | 150.0 |
| $K^+$ | [mmol/l] | 5.00 |
| $Cl^-$ | [mmol/l] | 105.0 |
| H-HEPES$^{(\pm)}$ | [mmol/l] | 19.0 |
| HEPES$^-$ | [mmol/l] | 22.5 |
| Acetate$^-$ | [mmol/l] | 24.9 |
| Lactate$^-$ | [mmol/l] | 3.10 |
| creatinine | [mmol/l] | 0.25 |
| pH (37° C.) | [pH-units] | 7.38 |

Possible variants for Cal 1 (acidic) and Cal 1 (alkaline):
Variant 1 (Cal 1): for the calibration of creatinine

TABLE 2

| Substance | | Cal 1 acidic | Cal 1 alkaline | Resulting solution after 1:1-mixture | | |
|---|---|---|---|---|---|---|
| NaCl | [mmol/l] | 150 | 98.4 | $Na^+$ | [mmol/l] | 150.0 |
| KCl | [mmol/l] | — | 10.0 | $K^+$ | [mmol/l] | 5.00 |
| HCl | [mmol/l] | 6.60 | — | $Cl^-$ | [mmol/l] | 132.5 |
| NaOH | [mmol/l] | — | 51.6 | Hepes$^-$ | [mmol/l] | 22.5 |
| H-HEPES$^{(\pm)}$ | [mmol/l] | 20 | 63.0 | H-HEPES$^{(\pm)}$ | [mmol/l] | 19.0 |
| Creatinine | [mmol/l] | 0.50 | — | Creatinine | [mmol/l] | 0.25 |
| pH (37° C.) | [pH-units] | 2.50 | 7.96 | pH (37° C.) | [pH-units] | 7.38 |

Variant 2 (Cal 1): for the calibration of creatinine

TABLE 3

| Substance | | Cal 1 acidic | Cal 1 alkaline | Resulting solution after 1:1-mixture | | |
|---|---|---|---|---|---|---|
| NaCl | [mmol/l] | 150 | 43.4 | $Na^+$ | [mmol/l] | 150.0 |
| Na-acetate | [mmol/l] | — | 55.0 | $K^+$ | [mmol/l] | 5.00 |
| KCl | [mmol/l] | — | 10.0 | $Cl^-$ | [mmol/l] | 105.0 |
| HCl | [mmol/l] | 6.60 | — | Acetate$^-$ | [mmol/l] | 27.5 |
| NaOH | [mmol/l] | — | 51.6 | Hepes$^-$ | [mmol/l] | 22.5 |
| H-HEPES$^{(\pm)}$ | [mmol/l] | 20 | 63.0 | H-HEPES$^{(\pm)}$ | [mmol/l] | 19.0 |
| Creatinine | [mmol/l] | 0.50 | — | Creatinine | [mmol/l] | 0.25 |
| pH (37° C.) | [pH-units] | 2.50 | 7.96 | pH (37° C.) | [pH-units] | 7.38 |

Variant 3: for the calibration of creatinine, glucose, lactate, urea (pH, $Na^+$, $Cl^-$, $PCO_2$)
(Cal 1) $K^+$ serves for checking, determining or controlling the mixing ratio

TABLE 4

| Substance | | Cal 1 acidic | Cal 1 alkaline | Resulting solution after 1:1-mixture | | |
|---|---|---|---|---|---|---|
| NaCl | [mmol/l] | 145.0 | 46.80 | Na$^+$ | [mmol/l] | 150.0 |
| Na-lactate | [mmol/l] | 6.0 | — | K$^+$ | [mmol/l] | 5.00 |
| NaHCO$_3$ | [mmol/l] | — | 47.2 | NH$_4^+$ | [mmol/l] | 0.05 |
| NaOH | [mmol/l] | — | 55.0 | Cl$^-$ | [mmol/l] | 107.2 |
| KCl | [mmol/l] | — | 10.00 | Lactate$^-$ | [mmol/l] | 3.00 |
| HCl | [mmol/l] | 12.45 | — | HCO$_3^-$ | [mmol/l] | 22.34 |
| NH$_4$Cl | [mmol/l] | 0.10 | — | Hepes$^-$ | [mmol/l] | 22.5 |
| H-HEPES$^{(\pm)}$ | [mmol/l] | 40.2 | 42.8 | H-HEPES$^{(\pm)}$ | [mmol/l] | 19.0 |
| Creatinine | [mmol/l] | 0.50 | — | Creatinine | [mmol/l] | 0.25 |
| Glucose | [mmol/l] | 10.0 | — | Glucose | [mmol/l] | 5.00 |
| Urea | [mmol/l] | — | 18.0 | Urea | [mmol/l] | 9.00 |
| pH (37° C.) | [pH-units] | 2.90 | 10.13 | pH (37° C.) | [pH-units] | 7.38 |
| | | | | PCO$_2$ (37° C.) | [mmHg] | 40.7 |

Possible variants for Cal 2:
Variant 1 (Cal 2): for the calibration of creatine, creatinine, glucose, lactate, urea and K$^+$.

TABLE 5

| Substance | | Cal 2 | Resulting solution components | | |
|---|---|---|---|---|---|
| NaCl | [mmol/l] | 97.0 | Na$^+$ | [mmol/l] | 150.0 |
| Na-lactate | [mmol/l] | 15.0 | K$^+$ | [mmol/l] | 5.00 |
| Na-acetate | [mmol/l] | 15.5 | NH$_4^+$ | [mmol/l] | 0.05 |
| NaOH | [mmol/l] | 22.5 | Cl$^-$ | [mmol/l] | 107.2 |
| KCl | [mmol/l] | 8.00 | Lactate$^-$ | [mmol/l] | 15.0 |
| NH$_4$Cl | [mmol/l] | 0.05 | Acetate$^-$ | [mmol/l] | 15.5 |
| H-HEPES$^{(\pm)}$ | [mmol/l] | 41.5 | Hepes$^-$ | [mmol/l] | 22.5 |
| Creatinine | [mmol/l] | 0.25 | H-HEPES$^{(\pm)}$ | [mmol/l] | 19.0 |
| Creatine | [mmol/l] | 0.42 | Creatinine | [mmol/l] | 0.25 |
| Glucose | [mmol/l] | 25.0 | Creatine | [mmol/l] | 0.42 |
| Urea | [mmol/l] | 27.0 | Glucose | [mmol/l] | 5.00 |
| | | | Urea | [mmol/l] | 9.00 |
| | | | PH (37° C.) | [pH-units] | 7.38 |

Variant 2 (Cal 2): for the calibration of creatine, creatinine and glucose.

TABLE 6

| Substance | | Cal 2 acidic | Cal 2 alkaline | Resulting solution after 1:1-mixture | | |
|---|---|---|---|---|---|---|
| NaCl | [mmol/l] | 150 | 101.7 | Na$^+$ | [mmol/l] | 150.0 |
| KCl | [mmol/l] | — | 10.0 | K$^+$ | [mmol/l] | 5.00 |
| HCl | [mmol/l] | 3.30 | — | Cl$^-$ | [mmol/l] | 132.5 |
| NaOH | [mmol/l] | — | 48.3 | Hepes$^-$ | [mmol/l] | 22.5 |
| H-HEPES$^{(\pm)}$ | [mmol/l] | 10 | 73.0 | H-HEPES$^{(\pm)}$ | [mmol/l] | 19.0 |
| Glucose | [mmol/l] | 50.0 | — | Glucose | [mmol/l] | 25.0 |
| Creatinine | [mmol/l] | 0.21 | 0.29 | Creatinine | [mmol/l] | 0.25 |
| Creatine | [mmol/l] | — | 0.50 | Creatine | [mmol/l] | 0.25 |
| pH (37° C.) | [pH-units] | 2.50 | 7.60 | pH (37° C.) | [pH-units] | 7.38 |

Washing and zero-point calibration solution („standby")

TABLE 7

| Substance | | Var. 1 | Var. 2 | Var. 3 |
|---|---|---|---|---|
| Creatinine | [mmol/l] | 0.00 | 0.00 | 0.00 |
| Creatine | [mmol/l] | 0.00 | 0.00 | 0.00 |
| H-HEPES$^{(\pm)}$ | [mmol/l] | 83.0 | 41.5 | 83.0 |
| NaOH | [mmol/l] | 45.0 | 22.5 | 45.0 |
| NaCl | [mmol/l] | 99.95 | 100.0 | 100.0 |
| Na-acetate | [mmol/l] | 4.05 | 26.5 | 40.0 |
| KCl | [mmol/l] | 5.00 | 5.00 | 5.00 |
| Urea | [mmol/l] | 1.00 | — | — |
| NH$_4$Cl | [mmol/l] | 0.05 | — | — |
| Na$_2$MgEDTA | [mmol/l] | 0.50 | 0.50 | 0.50 |
| Resulting equilibrium concentrations | | | | |
| Creatinine | [mmol/l] | 0.00 | 0.00 | 0.00 |
| Creatine | [mmol/l] | 0.00 | 0.00 | 0.00 |
| Na$^+$ | [mmol/l] | 150.0 | 150.0 | 186.0 |
| K$^+$ | [mmol/l] | 5.00 | 5.00 | 5.00 |
| Mg$^{++}$ | [mmol/l] | 0.50 | 0.50 | 0.50 |
| NH$_4^+$ | [mmol/l] | 0.05 | 0.00 | 0.00 |
| Cl$^-$ | [mmol/l] | 105.0 | 105.0 | 105.0 |
| H-HEPES$^{(\pm)}$ | [mmol/l] | 38.0 | 19.0 | 38.0 |
| HEPES$^-$ | [mmol/l] | 45.0 | 22.0 | 45.0 |
| Acetate$^-$ | [mmol/l] | 4.05 | 26.5 | 40.0 |
| Urea | [mmol/l] | 1.00 | 0.00 | 0.00 |
| NH$_4^+$ | [mmol/l] | 0.05 | 0.00 | 0.00 |
| EDTA$^{(4-)}$ | [mmol/l] | 0.50 | 0.50 | 0.50 |
| pH (37° C.) | [pH-units] | 7.38 | 7.38 | 7.38 |

TABLE 8

| Aqueous solution comprising 120 µM of creatinine and 210 µM of creatine | Creatinine sensor, calibrated under addition of acetate | Creatinine sensor, calibrated without addition of acetate | Difference | Creatine sensor, calibrated under addition of acetate | Creatine sensor, calibrated without addition of acetate | Difference |
|---|---|---|---|---|---|---|
| Without interfering substances | 234 µM of creatinine | 121 µM | 48% | 363 µM of creatine | 209 µM | 42% |
| +40 mmol/l of acetate | 124 µM | 68 µM | 45% | 211 µM | 133 µM | 37% |
| +25 mmol/l of bicarbonate | 152 µM | 80 µM | 47% | 266 µM | 161 µM | 39% |
| Mean value | | | 47% | | | 40% |

TABLE 9

| Aqueous solution comprising 230 µM of creatinine | Creatinine sensor, calibrated under addition of acetate | Creatinine sensor, calibrated without addition of acetate | Difference |
|---|---|---|---|
| Without interfering substances | 371 µM of creatinine | 225 µM | 39% |
| +40 mmol/l of acetate | 229 µM | 146 µM | 36% |
| +25 mmol/l of bicarbonate | 226 µM | 137 µM | 39% |
| Mean value | | | 38% |

TABLE 10

| Control agent | Creatinine content of the control agent | Creatine content of the control agent | Creatinine sensor, calibrated under addition of acetate | Creatinine sensor, calibrated without addition of acetate | Creatine sensor, calibrated under addition of acetate | Creatine sensor, calibrated without addition of acetate |
|---|---|---|---|---|---|---|
| Bovine serum | 97 µM | — | 72 µM | 34 µM | 249 µM | 157 µM |
| Autotrol 1 | 530 µM | 729 µM | 452 µM | 255 µM | 619 µM | 412 µM |
| Autotrol 2 | 176 µM | 242 µM | 138 µM | 82 µM | 220 µM | 137 µM |
| Autotrol 3 | 88 µM | 125 µM | 70 µM | 43 µM | 116 µM | 80 µM |

What is claimed is:

1. A method for calibrating a biosensor for the amperometric determination of creatinine in biological liquids, wherein the biosensor is integrated and operated in a device and has one electrode system each for measuring the concentrations of creatinine and creatine, with the electrode system for measuring the concentration of creatinine comprising creatininase, creatinase and sarcosine oxidase and the electrode system for measuring the concentration of creatine comprising creatinase and sarcosine oxidase, the method comprising:

mixing an acidic creatinine solution with an alkaline buffer to form a creatinine calibration solution;

calibrating the electrode system for measuring the creatine concentration with a creatine calibration solution wherein creatinine and creatine are at a thermodynamic equilibrium; and calibrating the electrode system for measuring creatinine concentration with the creatinine calibration solution, wherein the result of the electrode system for measuring the concentration of creatinine is corrected by the result of the electrode system for measuring the concentration of creatine.

2. The method of claim 1 wherein the acidic creatinine solution has a pH of 2 to 4.

3. The method of claim 2 wherein the acidic creatinine solution has a pH of 2.5 to 3.

4. The method of claim 1 wherein the creatinine concentration of the creatinine calibration solution is calculated by the use of an ionic tracer weighed into one of the acidic creatinine solution and the alkaline buffer.

5. The method of claim 1 further comprising adding an interfering substance present in the biological liquid to at least one of the calibration solutions at the average physiological concentration of the substance.

6. The method of claim 5 wherein the interfering biological substance is an enzyme inhibitor or an inhibitor having a similar effect on the enzyme as those present in the biological liquid.

7. The method of claim 5 wherein the inhibitor is acetate or bicarbonate.

8. The method of claim 1 further comprising adding one or more biocides to at least one of the calibration solutions.

9. The method of claim 8 wherein the one or more biocides comprise an isothiazolone derivative.

10. The method of claim 1 further comprising adding one or more antibiotics to at least one of the calibration solutions.

11. The method of claim 1 wherein the alkaline buffer solution comprises an amine buffer according to Norman Good.

12. The method of claim 1 wherein the alkaline buffer solution comprises a bicarbonate.

13. The method of claim 1 wherein the alkaline buffer solution comprises an amine buffer comprising sulfonic acid groups according to Norman Good.

14. The method of claim 1 wherein the alkaline buffer solution comprises lactate/lactic acid.

15. A method for calibrating a biosensor for the amperometric determination of creatinine in biological liquids, wherein the biosensor has one electrode system each for measuring the concentrations of creatinine and creatine, the method comprising providing a creatinine calibration solution and a creatine calibration solution for calibrating the electrodes, wherein the creatinine solution is prepared by mixing an acidic creatinine solution with an alkaline buffer solution, and the creatine calibration solution comprises a solution in which creatinine and creatine are at a thermodynamic equilibrium.

16. The method of claim 15 wherein the acidic creatinine solution has a pH of 2 to 4.

17. The method of claim 15 wherein the creatinine concentration of the creatine calibration solution is calculated by the use of an ionic tracer weighed into one of the acidic creatinine solution and the alkaline buffer.

18. The method of claim 15 further comprising adding interfering substances present in the biological liquids to be examined to at least one of the calibration solutions at their average physiological concentrations.

19. The method of claim 18 wherein the inhibitor is acetate or bicarbonate.

20. The method of claim 15 further comprising adding one or more biocides or antibiotics to at least one of the calibration solutions.

\* \* \* \* \*